United States Patent
Ecker et al.

(10) Patent No.: US 8,492,609 B2
(45) Date of Patent: *Jul. 23, 2013

(54) ABSORBENT ARTICLE WITH PRINTED LAYER

(75) Inventors: Cornelia Ecker, Sulzbach (DE); Ivano Gagliardi, Pescara (IT); Paolo Veglio, Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/123,663

(22) Filed: May 20, 2008

(65) Prior Publication Data

US 2008/0294139 A1    Nov. 27, 2008

(30) Foreign Application Priority Data

May 25, 2007    (EP) .................................. 07108950

(51) Int. Cl.
*A61F 13/15*    (2006.01)
*A61F 13/20*    (2006.01)

(52) U.S. Cl.
USPC ..................................... 604/367; 604/385.01

(58) Field of Classification Search
USPC .......... 604/367, 380, 385.01, 385.03, 385.23, 604/387
See application file for complete search history.

(56) References Cited

U.S. PATENT DOCUMENTS

| | | | |
|---|---|---|---|
| 6,307,119 B1 | 10/2001 | Cammarota et al. | |
| 6,569,136 B1 | 5/2003 | Tao et al. | |
| 6,949,689 B2 | 9/2005 | Noda et al. | |
| 6,972,010 B2 * | 12/2005 | Pesce et al. | 604/289 |
| 2002/0007162 A1 * | 1/2002 | Cammarota et al. | 604/361 |
| 2004/0170813 A1 | 9/2004 | Digiacomantonio et al. | |
| 2005/0101931 A1 | 5/2005 | Bryant et al. | |
| 2005/0192549 A1 * | 9/2005 | Veglio et al. | 604/367 |
| 2006/0111684 A1 | 5/2006 | Berba et al. | |
| 2006/0129116 A1 | 6/2006 | Hughes et al. | |
| 2006/0142710 A1 | 6/2006 | Kigata et al. | |
| 2006/0149197 A1 | 7/2006 | Niemeyer | |
| 2007/0093770 A1 | 4/2007 | Ecker et al. | |
| 2007/0100308 A1 | 5/2007 | Miyairi | |

FOREIGN PATENT DOCUMENTS

| | | |
|---|---|---|
| DE | 29824115 U1 | 6/2000 |
| EP | 1693034 A1 | 8/2006 |
| EP | 1779874 A1 | 5/2007 |
| EP | 1994918 A1 | 11/2008 |
| JP | 2000-279442 A | 10/2000 |
| JP | 2002360620 A | 12/2002 |
| JP | 2003-199786 A | 7/2003 |
| JP | 2005185858 A | 7/2005 |
| WO | 9715261 A1 | 5/1997 |
| WO | WO 2004/006818 A1 | 1/2004 |
| WO | WO 2005084597 A1 * | 9/2005 |
| WO | 2006050095 A1 | 5/2006 |

OTHER PUBLICATIONS

PCT International Search Report dated Sep. 18, 2008.

* cited by examiner

*Primary Examiner* — Michele M Kidwell
(74) *Attorney, Agent, or Firm* — Andrew J. Hagerty; Megan C. Hymore; Amanda T. Barry

(57) ABSTRACT

A feminine hygiene article with a topsheet, a backsheet, and an absorbent core placed between the topsheet and the backsheet. The article may include a printed pattern which is printed on a garment-facing side of the backsheet. The printed pattern is visible through at least a portion of topsheet outside a core area.

1 Claim, 4 Drawing Sheets

ABSORBENT ARTICLE WITH PRINTED LAYER

FIELD OF THE INVENTION

The present invention is directed to feminine hygiene articles, for example articles commonly designated as "pantiliners".

BACKGROUND OF THE INVENTION

Feminine hygiene articles for collecting bodily fluids and other excretions from the pudental region of the feminine anatomy have been commercially proposed for many years. Feminine hygiene articles such as tampons or menstruating pads have originally been used for collecting excretions such as menses during the menstruating period. Articles commonly designated as pantiliners have also been proposed with the aim to provide protection of the wearer's undergarment from lighter soiling, for example at the beginning or the end of the menstruating period when the flow is lighter or even outside the menstruating period, for example to absorb daily vaginal discharge or slight urine leak.

Pantiliners normally require a lesser absorbency capacity than other absorbent products, mainly because they have to deal with lesser amount of fluid than purely menstrual absorbent articles or adult incontinence products. Pantiliners are therefore normally thinner compared to other absorbent articles such as sanitary pads. Some pantiliners are of a relatively simple construction, including a topsheet, an absorbent core and a backsheet. More complicated and costly constructions including further layers have been proposed, for example including a secondary topsheet and/or a secondary backsheet.

Absorbent articles having a core substantially smaller than the topsheet have been commercially proposed. For example the Procter & Gamble Company markets a pantiliner under the tradename Discreet® which has an oval shaped core within a generally "dog-bone" shaped article.

WO2004/00618A1 discloses an absorbent article having a graphic visible through the body contacting surface of the article. The graphic is printed either on the body facing surface of the garment contacting layer or on the garment facing surface of the body contacting layer.

Side leakage, i.e. the leakage of previously absorbed liquid through the side edges of the core of the articles, is a common problem in the field of feminine hygiene articles. Attempts have been made in the past to solve or mitigate this problem, in particular by providing physical barriers to the progression of the liquid in the outward direction, see for example WO2004/060242A1. However, these systems add costs and have not been widely adopted. It is therefore common for the users to check from time to time the progression of the absorbed fluid within the article and replace the article by a new one when the absorbed liquid is approaching the edges of the absorbent core.

However, it was found that it can be difficult for the user to determine where the limit of the core lay within the envelope formed by the backsheet and topsheet for the articles discussed above, where the surface of the core is smaller than the overall surface of the article, and in particular for these articles where the core itself is very thin. These conditions may create the problem that the user can no longer easily determine when the maximum capacity of the absorbent core is approached and therefore may not change the article before side leakage occurs. This may be an acute problem for thin articles which have a smaller absorbent capacity than other products. Alternatively, the user may also be induced to change the article prematurely, in fear that the liquid may be approaching one of the edges of the core.

There is therefore a need for feminine hygiene articles which are discrete, relatively cheap to manufacture and still have good fluid handling capacity. Such articles should also allow the consumer to detect when the absorbed liquid is approaching the edges of the core.

SUMMARY OF THE INVENTION

The present invention is for a feminine hygiene article comprising a topsheet, a backsheet, and an absorbent core placed between the topsheet and the backsheet. The core defines a core area on the surface of the topsheet. The core area is substantially smaller than the surface of the topsheet. The backsheet of the article is printed on its garment facing side with a printed pattern. The printed pattern is visible at least through a portion of the area of the topsheet which is outside the core area of the topsheet.

BRIEF DESCRIPTION OF THE DRAWINGS

While the specification concludes with claims which particularly point out and distinctly claim the invention, it is believed that the present invention will be better understood from the following description of preferred embodiments taken in conjunction with the accompanying drawings, in which like reference numerals identify identical elements and in which:

DETAILED DESCRIPTION OF THE INVENTION

While the specification concludes with claims which particularly point out and distinctly claim the invention, it is believed the present invention will be better understood from the following description.

As used herein, the term "feminine hygiene article" refers to the category of disposable absorbent articles used externally by women for collecting vaginal discharges and/or urine leaks and protecting their undergarment from soiling, and in particular pantiliners. These articles are normally sold to the consumer either in a folded or a non-folded (flat) configuration. Feminine hygiene articles are typically held in place adjacent the user's pubic region by the user's undergarment, to which they can be affixed via a releasable adhesive or other joining means.

Figure 1:
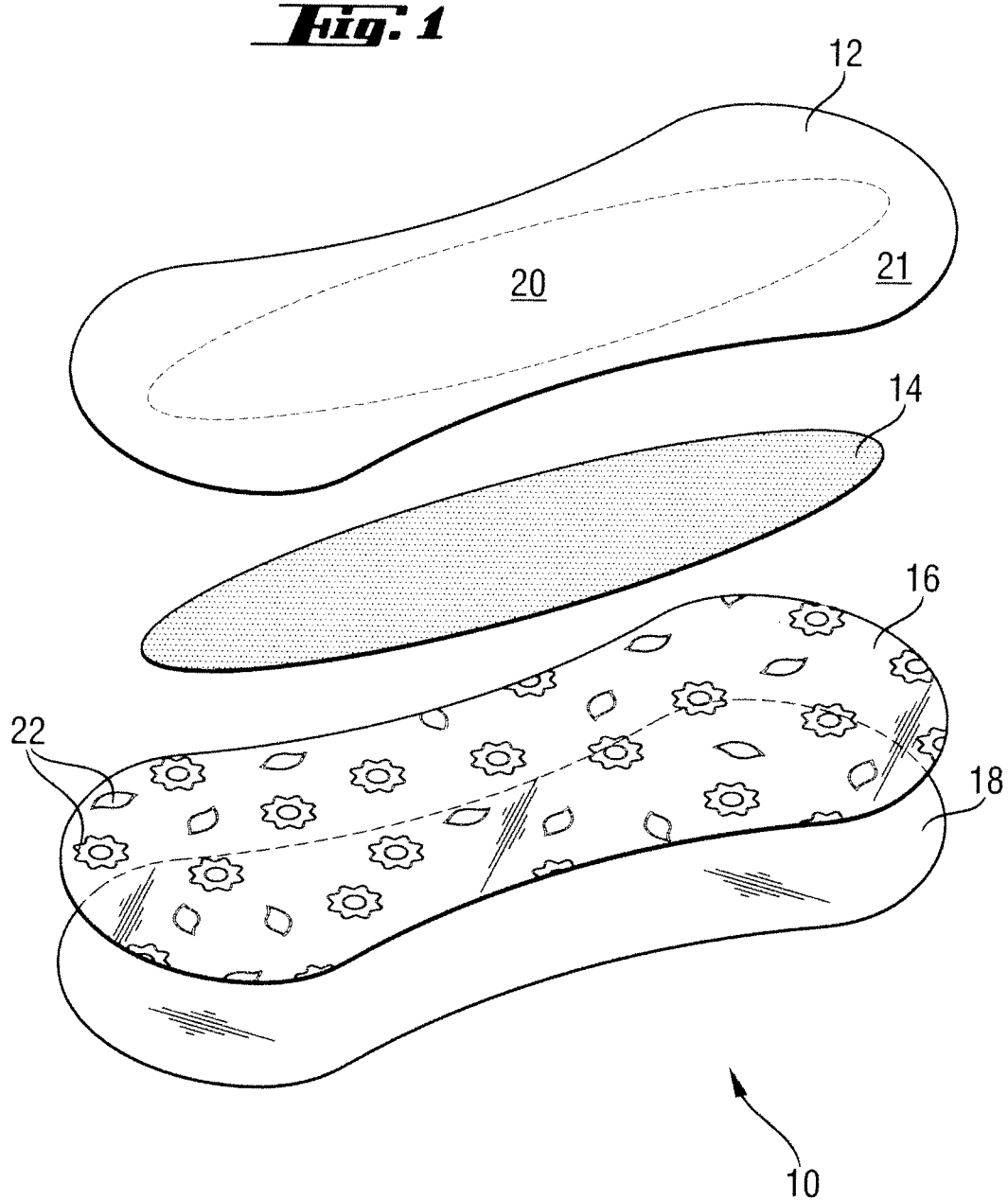
FIG. 1 is an exploded perspective view of a pantiliner according to the invention.
Figure 2:
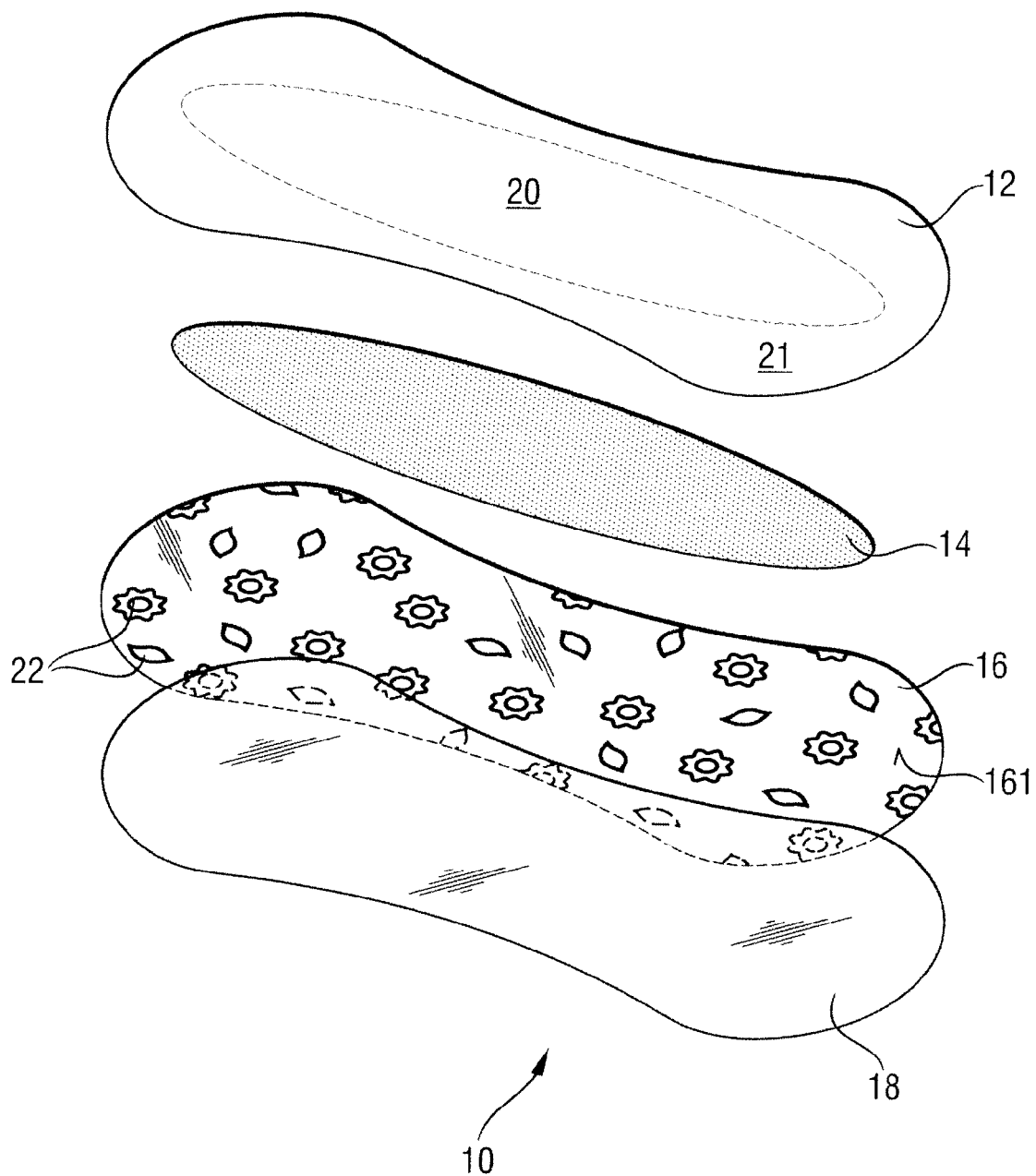
FIG. 2 is an exploded perspective view of the pantiliner of FIG. 1 from a different angle.
Figure 3:
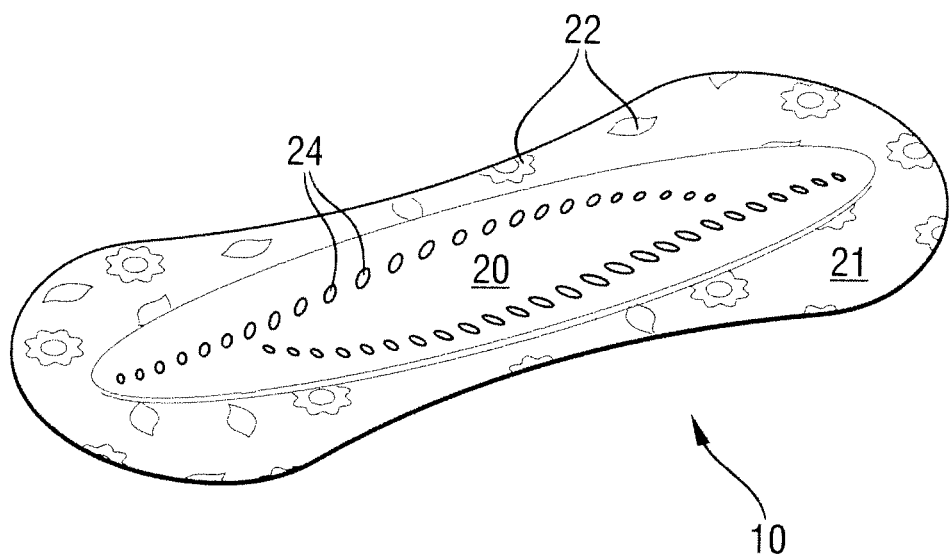
FIG. 3 is a perspective view of the pantiliner of FIG. 1.
Figure 4:
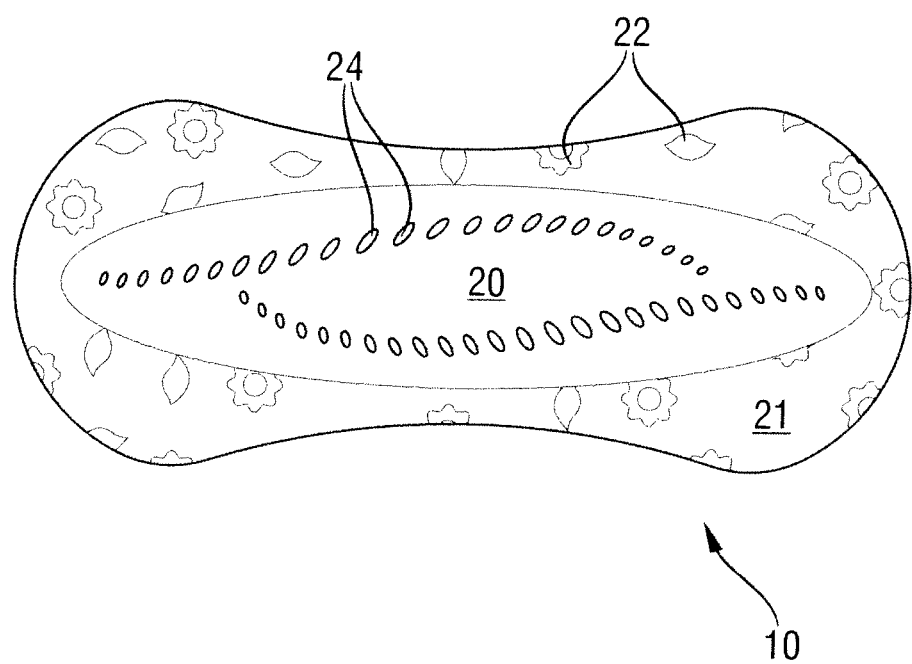
FIG. 4 is a top view of the pantiliner of FIG. 1.

Referring now to FIG. 1, a feminine hygiene article 10 is depicted in an exploded view comprising, from top to bottom, the following layers: a topsheet 12, an absorbent core 14, and a backsheet 16. A releasable cover 18 which may be present to cover an adhesive material on the outer-surface of the backsheet layer is also represented. The "top" of article is defined herein as the surface of the article oriented towards the user's body when in use, and the "bottom" is defined herein as the opposite surface of the article, i.e. the surface that will contact the woman's undergarment. As used herein, the term "core area" refers to the area 20 of the topsheet 12 directly overlying the absorbent core 14.

The releasable cover 18 is discarded by the user when the absorbent product is placed in the undergarment and is also discarded for the purpose of measuring the thickness of the article.

Absorbent Core 14

The articles of the invention comprises an absorbent core 14 placed between the topsheet 12 and the backsheet 16. As used herein, the term "absorbent core" refers to a material or combination of materials suitable for absorbing, distributing, and storing fluids such as urine, blood, menses, and/or other body exudates.

The size and shape of the absorbent core 14 is such that the core area 20 has a substantially smaller surface than the topsheet of the article. By "substantially smaller", we mean that the surface of the core area 10 is at least about 10% smaller than the surface of the topsheet 12. The topsheet 12 may be contiguous with the backsheet 16. The absorbent core 14 may be generally centered in the middle of the article, and may be disposed away from the periphery of the article to provide improved flexibility along the edges of the article.

By providing an absorbent core having a substantially smaller surface than the topsheet, several benefits are achieved. The amount of core material used is reduced, lowering the overall costs of manufacturing the product. A core having a smaller surface also increases the overall flexibility of the product, because the regions of the product not provided with a core are generally less rigid than the region where the core is situated.

The absorbent core 14 may have an oval shape as represented in the figures but may also have any other shape. For example it is typical for absorbent cores to be rectangularly shaped for ease of manufacturing. However flexibility may be better with cores having a curved shape and not comprising right angles.

The ratio of the surface of the core area to the surface of the topsheet 12 may desirably be comprised within any of the following ranges: between about 20% and about 90%, between about 30% and about 70%, and between about 40% and about 60%. The surface of the topsheet 16 encompasses the core area 20, which is part of the surface of the topsheet. The surface of the topsheet is the sum of the surface of the core area 20 and the area 21 of the topsheet 16 outside the core area 20.

The absorbent core 14 can be made of any suitable materials. Non-limiting examples of suitable liquid-absorbent materials include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The absorbent core comprise superabsorbent polymer (SAP), normally distributed within a matrix of cellulosic fibers, for example in order to reduce the thickness of the absorbent core.

The absorbent core may be unitary, or may be a laminate of two or more layers. For example, the core may comprise a fluid impermeable barrier layer (e.g. a PE Patch) on its backsheet-facing side to prevent fluids retained by the absorbent core from striking through the pantiliner and soiling adjacent garments. An exemplary PE patch is a 25 gsm poly film available form Britton Taco (UK) under trade name ST-012A-White.

Further generic information regarding absorbent cores can be found in prior patent publications, see for example WO0207662A1 and WO9119471.

Printed Pattern 22

Commercially available feminine hygiene articles often have a substantially overall white appearance. In the case of articles having an absorbent core with a surface substantially smaller than the surface of the topsheet, it may be difficult for some users to distinguish the limit of the core, and thus difficult to assess when the absorbed liquid is approaching the side of the core, and when the article should be changed to prevent side leakage. This is particularly a problem for relatively thin article having a thickness of less than about 5 mm.

A solution to this problem is to provide a visual contrast between the area of the topsheet directly overlying the absorbent core, herein designated as core area 20, and at least a portion of the area 21 of the topsheet outside the core area, i.e. at least a portion or all of the rest of the surface of the topsheet facing the user when the article is in place. This visual contrast helps the user to easily determine the periphery of the absorbent core within the article.

A cost-effective way to produce this contrast between the core area 20 of the topsheet 14 and an area of the topsheet 21 outside the core area 20, is to provide the backsheet 16 with a printed pattern 22. It is possible to print the pattern 22 on the garment-facing side 161 of the backsheet 16 (i.e. the side of the backsheet facing outwardly) without significant issues.

One potential advantage of printing on the garment-facing side 161 of the backsheet 16 is that it increases the visibility of the printed pattern 22 through the release cover 18 (which may be transparent or translucent). This may create a "printed like" release cover effect. Having the backsheet 16 with the printed pattern 22 printed on its garment-facing side 161 may render it superfluous to print the release cover 18 itself to avoid pattern overlapping and additional cost. Another possible advantage is that when the articles in a packaged in a bag or box with a window, the consumer may be to better able to identify the printed pattern from the carton box/bag provided.

Because conventional core materials are normally not transparent, but often substantially opaque, the printed pattern 22 is not, or at least much less visible, through the core area 20 than through the area of the topsheet 21 which is outside of the core area 20. The printed pattern 22 is however visible by transparency through at least a portion of the surface of the topsheet 21 which is outside the core area 20. By "visible", we mean that a subject having a good vision in both eyes (10/10) holding the article at a distance of about 50 cm in a brightly lit room with incandescent light can see the printed pattern 22. On the other hand, conventional topsheet and backsheet layers are normally substantially transparent or translucent so that the printed pattern is visible on the body-facing side of the article by transparency through these layers outside the core area.

The surface coverage of the printed pattern 22 on the backsheet 16 may vary. It may be desirable to have a surface coverage ranging from about 2% to about 40% of the total surface of the backsheet layer. Below about 2%, the printed area may not be large enough to be helpful to provide the visual contrast between the core area 20 and at least a portion of the remaining area 21 of the topsheet 12. Above about 40% surface coverage, the increased costs due to the increased amount of ink used are detrimental. Advantageously, a surface coverage of between about 8% and about 25% may be selected, providing a good cost-benefits balance, but none of these ranges should be considered limiting.

Figure 5:
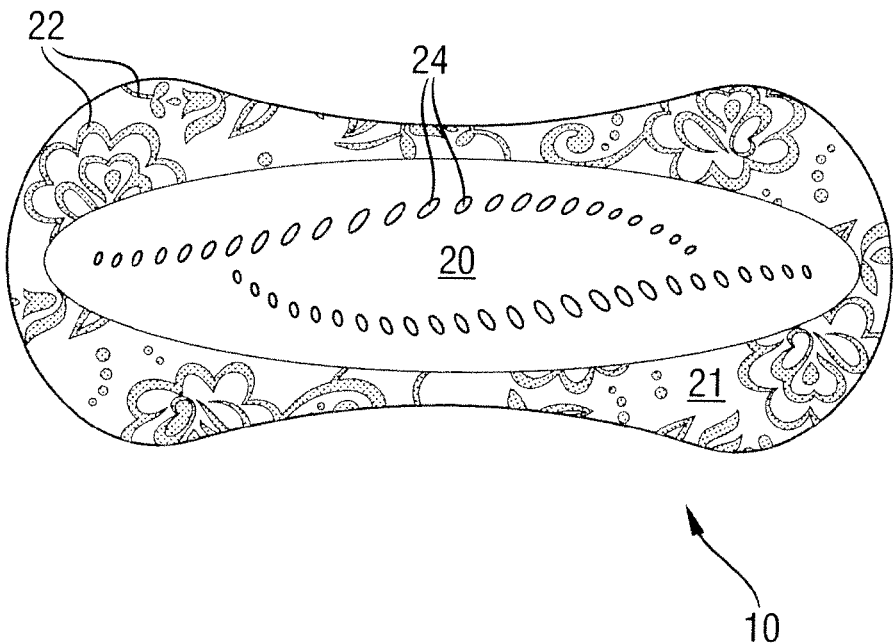
FIG. 5 is a top view of another embodiment of the invention.

The printed pattern 22 may comprise, as represented in FIG. 1, a series of dispersed discrete printed elements which may be identical or differ within the printed pattern 22. Of course, other discrete elements than those represented may be used, for example floral decorative elements (flowers, leaves), stars, or any other decorative elements. Further are as shown on FIG. 5 and FIG. 6. The printed pattern 22 may also consist of a continuous element rather than discrete elements.

The printed pattern 22 may be printed on the backsheet layer 16 with any conventional printing method, such as flexo print or roto gravure printing. The printed pattern 22 should be printed with an ink sufficiently strong to be visible through at least a portion of the topsheet 21 of the article outside the core area 20. A black ink may be used, but it may be preferred to use a coloured ink such as pink, violet, green, purple, blue or yellow, or even a combination of different coloured inks. By "printed pattern" we primarily mean a visible pattern obtained by a conventional ink printing method discussed above. The term "printed pattern" also encompasses patterns obtained by less usual techniques but that provide the same or a similar effect, for example it may possible to provide a similar visual effect by heat crimping a plastic nonwoven layer (e.g. backsheet) so that the crimped area, which then becomes translucent, provides a similar visual effect as an ink printed area. For example, if the panty of the user is colored, the color of panty will be more visible through the crimped zone.

Although not required by the invention, an ink with hydrophobic character may be desirable to prevent the ink from "drawing" fluids away from the core. Many commercial inks are solvent-based and therefore capable of providing a hydrophobic effect. In addition, hydrophobic agents such as oils or waxes may be added to the commercial ink composition if desired. A "solvent-based" ink does not use water as the mobile phase to carry various pigments, resin(s) or binder(s), and additives, such as wax. Typically, "solvent-based" inks use one or more of various organic solvents such as alcohols, esters, aliphatics, and aromatics to solubilize these components. Solvents that solubilize resins well are generally referred to as "active", while those that are not "active" are called "diluents. Solvent-based inks that typically use aliphatic hydrocarbons with common binder types, such as polyamide, shellac, rosin esters, nitro-cellulose, and styrene maleic are suitable for use herein. Examples of suitable inks are supplied by Sunchemical/Hartmann Niederhausen/TS under the trade name P-3228/811 PMS 270 Lavender or trade name V8185/811 PMS 382 Green.". A "water-based" ink typically uses water predominantly as the mobile phase. Water-based inks may also be suitable for the invention if they do not substantially negative impact on the product's performance.

Backsheet 16

The backsheet 16 may be made of any suitable material, for example any standard backsheet materials. These materials are generally flexible, liquid resistant, and liquid impervious. The general function of the backsheet is to prevent discharges absorbed by the core from escaping the sanitary napkin and soiling the clothing and bedding of the wearer.

Any conventional backsheet materials may be used within the invention, such as polyolefinic films or nonwoven webs. Nonwovens webs may be advantageous because they normally provide better breathability for the articles and may be cheaper than polyolefinic films. For example, a relatively hydrophobic 23 grams per square meter (gsm) spunbonded nonwoven web of 4 denier polypropylene fibers available from BBA Neuberger (Italy) may be used.

Topsheet 12

The topsheet 12 is the layer of the article which is oriented towards and contacts the body of the wearer, and is therefore the first layer to receive the bodily discharges. The topsheet is normally made of a single layer, as represented in the Figures, but may also comprises more than one layer (for example a central topsheet layer and two overlapping lateral stripes, as disclosed in WO93/09744 or EP766,953).

The topsheet 12 is normally liquid pervious. The term "liquid pervious" as used herein refers to components that allow liquids to pass therethrough without significantly retarding or obstructing the transmission of such liquids therethrough.

It is envisaged that any conventional topsheet materials may be used within the invention, as long as the material is not completely opaque. Suitable topsheets may be made from nonwoven materials or perforated polyolefinic films. An exemplary topsheet suitable for use herein is a relatively hydrophobic 20 gsm spunbonded nonwoven web comprising bicomponent fibers of the sheath core type (PP/PE) available from Pegas a.s., Czech Republic.

If desired, the topsheet 12 may be sprayed with a surfactant to enhance liquid penetration to the core. The surfactant is typically non-ionic and should be nonirritating to the skin. A surfactant density of about 0.01 milligrams per square centimeter of topsheet area is normally suitable. An exemplary surfactant is sold by the Glyco Chemical, Inc. of Greenwich, Conn. as Pegosperse 200 mL. The topsheet may have a plurality of apertures to permit liquids deposited thereon to pass through to the core more quickly.

The topsheet 12 and the backsheet 16 are preferentially peripherally joined using known techniques. The layers of the articles may also be glued to each other.

Embossed Pattern 24

The articles of the invention may advantageously present an embossed pattern 24. Embossing may normally serve several functions, such as providing a bonding between overlying layers and/or providing a quicker fluid pathways through the topsheet towards the core. Ideally, the embossing may also be aesthetically pleasing. The embossed pattern can be achieved with standard techniques such as thermal bond, ultrasonic bond or pressure. A suitable process is thermal bonding wherein the layers are passed through two steel rolls where one is engraved with the visual pattern and the other is flat. Both rolls are warmed to temperature suitable to melt the layer (typical range from 90 to 170° C.). The embossed pattern may be partially or entirely comprised within the core area. This may further increase the distinctiveness of the core 20 area compared to the rest of the topsheet 21.

Figure 6:
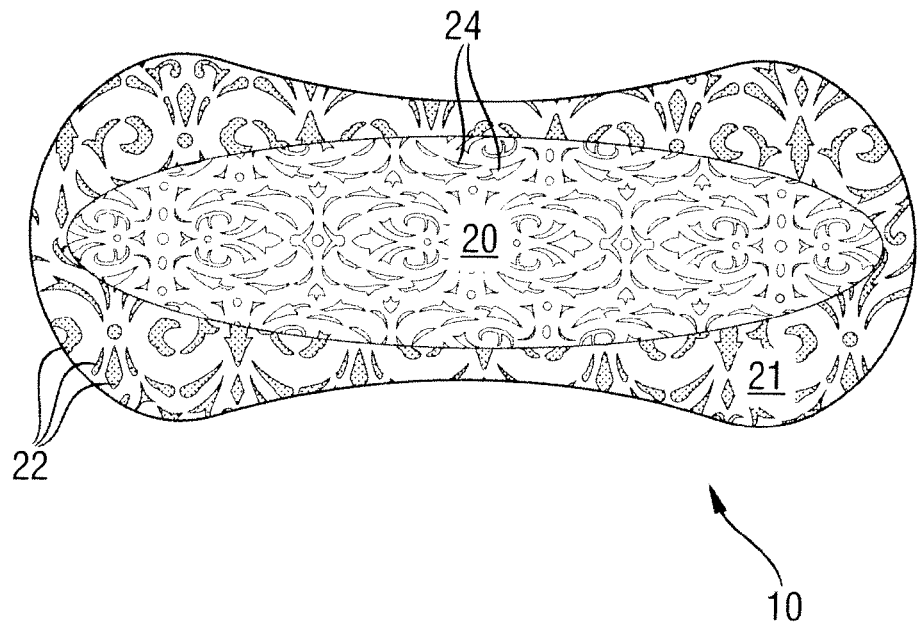
FIG. 6 is a top view of yet another embodiment of the invention.

The embossing roll may be engraved using conventional techniques such as machine tooling for most embossed patterns, but it may be preferred to use acid etching or laser engraving to provide a finer engraving, and thus a finer embossed pattern, for example as represented in FIG. 6.

Releasable Cover 18

The garment facing side 161 of the backsheet 16 may comprise means for attaching the article 10 to the undergarment of the wearer. Pressure sensitive adhesives have been commonly found to work well for this purpose. It is usual to use one or two strips of longitudinally oriented adhesive to provide good protection against either the front or the back of the sanitary napkin becoming detached from the wearer's undergarment. The adhesive strip may be continuous or intermittent. For example two longitudinally oriented strips, one on each side of the longitudinal centerline, may be applied.

Full coverage of the backsheet may also be applied. The adhesive may be applied via direct slot coating application process. A so called "finger lift", such a small area of the backsheet where no adhesive are applied and where the release cover is not attached to the backsheet, may also be provided to ease the removal of the releasable cover by the user.

The adhesive coated on the backsheet surface is typically provided with a releasable protective cover 18, which is removed at the point of use by the user. The releasable cover may be a silicone coated release paper, a plastic film or any other easily removable cover. The releasable cover may be in a single piece or in a multitude of pieces, e.g. to cover the individual adhesive areas and protect them from contamination. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany.

As indicated above, one potential advantage of printing on the garment-facing side 161 of the backsheet 16 is that it increases the visibility of the printed pattern 22 through the release cover 18 (which may be transparent or translucent). This may create a "printed like release paper effect".

General

The thickness of the absorbent articles according to the invention may advantageously be relatively small compared to many other feminine absorbent articles such as conventional sanitary pads. The articles of the invention have a thickness (also called "caliper") of less than about 5 millimeters, as measured using the standard test described below. Desirably, the articles may be even thinner, to provide very discrete articles. The lowest limit for the thickness of the article will be dictated by technical feasibility, but obtaining an effective article thinner than 0.4 mm may be difficult. Suitable thickness ranges for the articles of the invention include of from about 0.4 mm to about 4 mm, and from about 0.6 mm to about 3 mm. As used herein, the term "thickness of the article" refers to the thickness value measured in the center of the article, i.e. normally including the thickness of the core 14.

The dimensions of the articles of the invention in the horizontal plane are typical of the articles in the field. For example the length of such products will normally lie in a range of from about 8 cm to about 20 cm for the length of the article, and of from about 3 to about 9 cm for its width. The overall surface of the article (so typically the surface of the topsheet) may also lie within the usual range found for these articles, which normally would be of from about 40 $cm^2$ to about 250 $cm^2$. For the purpose of providing exemplary dimensions of a pantiliner such as the one represented in the Figures, such a pantiliner may have a length of 15 cm, a width (at center) of 4.8 cm, an overall surface of the article of 79 $cm^2$ and a core area surface of 38 $cm^2$. An exemplary thickness of the article represented is 0.9 mm.

The article may or may not comprise so-called "wings", which are side-wrapping elements destined to be folded around the undergarment. These wings are however normally used for sanitary pads and are not normally present for thinner products such as pantiliners.

The articles of the invention are normally disposable, i.e. are not intended to be re-usable or washable but are normally disposed of after use.

Method of Manufacture

The sanitary articles of the present invention may be produced industrially by any conventional means. The different layers may thus be assembled using standard means such as embossing (e.g. thermal bonding) or gluing or a combination of both. The converting line may comprise a printed step wherein the ink is applied to the backsheet of the article. It may however by simpler to carry the printed step on the backsheet outside the converting line of the article, before this layer is joined with any of the other layers.

Thickness Measurement

The articles of the inventions may be relatively thin and not bulky, so that the thickness measurements will be less dependent of the pressure applied when making the measurement, than for example for bulky articles such as thick pads. The following specific method is used to measure the thickness of the article of the invention. The equipment may comprise an apparatus capable of measuring thickness with a 0.01 mm tolerance. A commercial supplier of such equipment is for example Ono Sokki (www.onosokki.net), for example their Caliper Gauge GS-503 and digital readout DG 2610 may be used. The caliper gauge is fitted with a foot, which may have an exemplary 24.13 mm diameter. A suitable pressure exerted when the measurement is made is 0.689 kPa.

The test procedure is as follows. Make sure the micrometer is zeroed. Place the article without the release cover on the base plate, the topsheet facing up. If the article was provided in a compressed state (as is sometimes the case in certain packaging), the article is let to rest about 10 mn before its thickness is measured. Similarly, if the article was provided folded, the article is first opened and let about 10 nm to rest in its "flat" shape. Position the article on the base plate so that when the foot is lowered, it is in the center of the article. Let the foot gently lowers itself onto the article at a rate of 5 mm/sec+/−2 mm/sec. Determine the article caliper by reading the micrometer dial 10 seconds after the foot comes to rest. The shaft and foot should deliver approximately 32 grams of force for a pressure of 0.69+/−0.02 kPa to the sample with the above mentioned foot having a diameter of 24.13 mm.

What is claimed is:

1. A feminine hygiene article comprising:
   i) a nonwoven topsheet;
   ii) a nonwoven backsheet;
   iii) an absorbent core placed between the topsheet and the backsheet;
   iv) a fluid impermeable barrier layer placed between the core and backsheet;
   v) a printed flower pattern, and
   vi) an embossed flower pattern;
   wherein the absorbent core defines a core area on a surface of the topsheet which is smaller than the surface of the topsheet, wherein the surface of the core area is between about 30% and about 70% of the surface of the topsheet,
   wherein the embossed pattern is located within the core area,
   wherein the printed pattern is printed on the backsheet, wherein the printed pattern covers the majority of the backsheet, including the portions of the backsheet which are located under the core area,
   wherein the printed pattern is printed with an hydrophobic ink,
   wherein said printed pattern is visible on the garment facing side of the backsheet as well as through at least a portion of an area of the body facing side of the topsheet which is outside the core area;

wherein said printed pattern is not visible through the core area;

wherein an adhesive is applied to the garment facing side of the backsheet, wherein a releasable cover covers the adhesive, wherein the adhesive is not applied to a finger lift portion of the backsheet such that the releasable cover is not attached to the backsheet at the finger lift portion;

wherein said article is a pantiliner; and wherein the printed pattern is visible through the releasable cover.

* * * * *